US008194963B2

(12) United States Patent
Shinagawa et al.

(10) Patent No.: US 8,194,963 B2
(45) Date of Patent: Jun. 5, 2012

(54) EFFICIENT ESTIMATOR OF PHARMACOKINETIC PARAMETERS IN BREAST MRI

(75) Inventors: Yoshihisa Shinagawa, Downingtown, PA (US); Vandana Mohan, Atlanta, GA (US); Gerardo Hermosillo Valadez, West Chester, PA (US); Bing Jian, Exton, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 659 days.

(21) Appl. No.: 12/399,288

(22) Filed: Mar. 6, 2009

(65) Prior Publication Data

US 2009/0238428 A1   Sep. 24, 2009

Related U.S. Application Data

(60) Provisional application No. 61/035,172, filed on Mar. 10, 2008.

(51) Int. Cl.
*G06K 9/00* (2006.01)
(52) U.S. Cl. ........................................ 382/131; 382/128
(58) Field of Classification Search .................. 382/128, 382/131; 600/420
See application file for complete search history.

(56) References Cited

U.S. PATENT DOCUMENTS

| 6,322,770 | B1 * | 11/2001 | Rajopadhye et al. | ........ | 424/1.65 |
| 2009/0034814 | A1 * | 2/2009 | Shinagawa et al. | ........... | 382/131 |

OTHER PUBLICATIONS

Vandana Mohan, Yoshihisa Shinagawa, and Gerardo Hermosillo, "Expanded Pharmacokinetic model for population studies in Breast MRI," Medical imaging 2008 : Computer-aided diagnosis, Maryellen L. Giger, Nico Karssemeijer, Editors, Proc. SPIE, vol. 6915, 69150K (2008); Proceedings, Feb. 19, 2008.*
Tofts PS, Brix G, Buckley DL, Evelhoch JL, Henderson E, Knopp MV, Larsson HB, Lee TY, Mayr NA, Parker GJ, Port RE, Taylor J, Weisskoff RM, "Estimating kinetic parameters from dynamic contrast-enhanced T(1)-weighted MRI of a diffusable tracer: standardized quantities and symbols", J Magn Reson Imaging 1999, 10(3), 223-232.*
Thomas E. Yankeelov, Jeffrey J. Luci, Martin Lepage, Rui Li, Laura Debusk, P. Charles Lin, Ronald R. Price, John C. Gore, "Quantitative pharmacokinetic analysis of DCE-MRI data without an arterial input function: a reference region model", Magnetic Resonance Imaging, vol. 23, Issue 4, May 2005, pp. 519-529, ISSN 0730-725X.*
Port RE, Knopp MV, Hoffmann U, Milker-Zabel S, Brix G, "Multicompartment analysis of gadolinium chelate kinetics: blood-tissue exchange in mammary tumors as monitored by dynamic MR imaging", J Magn Reson Imaging. Sep. 1999;10(3):233-41.*
Vandana Mohan, Yoshihisa Shinagawa, Bing Jian, and Gerardo Hermosillo Valadez, "Robust pharmacokinetic analysis for population studies in breast cancer detection using the Mohan-Shinagawa model," Proceedings of the First Workshop on Analysis of Functional Medical Images, 2008, 121-128.*

* cited by examiner

*Primary Examiner* — Tony Ko
*Assistant Examiner* — Jori S Reilly-Diakun
(74) *Attorney, Agent, or Firm* — Peter Withstandley

(57) ABSTRACT

A method for performing pharmacokinetic analysis in magnetic resonance (MR) images includes administering a dose of contrast agent (CA) into a subject. A sequence of medical images is acquired of the subject at set temporal intervals. The time-based behavior of concentrations of CA is described within the subject for each voxel of each medical image of the sequence of medical images based on a reference voxel using a compartmental model for pharmacokinetic analysis that is based on a set of compartmental model parameters. The compartmental model is solved for each of the compartmental model parameters. The solution for the compartmental model parameters is used to estimate one or more parameters of physiological significance.

17 Claims, 2 Drawing Sheets

EFFICIENT ESTIMATOR OF PHARMACOKINETIC PARAMETERS IN BREAST MRI

CROSS-REFERENCE TO RELATED APPLICATION

The present application is based on provisional application Ser. No. 61/035,172, filed Mar. 10, 2008, the entire contents of which are herein incorporated by reference.

BACKGROUND OF THE INVENTION

1. Technical Field

The present disclosure relates to magnetic resonance imaging (MRI) and, more specifically, to an efficient estimator of pharmacokinetic parameters in breast MRI.

2. Discussion of Related Art

Magnetic resonance imaging (MRI) is a medical imaging technique in which a human subject can be imaged in three-dimensions with a great deal of detail pertaining to the differentiation of different forms of bodily soft tissue. Thus MRI is well suited for the visualization and diagnosis of the human breast. In MRI, the human subject is exposed to a powerful magnetic field which aligns the nuclear magnetization of hydrogen atoms in water within bodily tissues. Radiofrequency fields are used to systematically alter the alignment of this magnetization and the hydrogen nuclei then produce a rotating magnetic field detectable by the scanner.

Structural image data may be generated from the received data signals to construct an image of the body. For example, the structural image may be generated from a number of spatial frequencies at different orientations. Frequency and phase encoding are used to measure the amplitudes of a range of spatial frequencies within the object being imaged. The number of phase-encoding steps performed may be selected to determine how much imaging data may be collected.

As MRI uses magnetic and radiofrequency fields to perform visualization, the patient is not exposed to potentially hazardous ionizing radiation as would be the case with CT scans.

While the MRI may be used to differentiate between various types of soft tissue, it may be difficult to precisely differentiate between benign and malignant lesions that are found within the human breast.

A magnetic contrast agent, such as one based on chelates of gadolinium may be administered to the patient subject prior to the acquisition of the MRI. As the contrast agent may be easily observed from the MRI, injecting the magnetic contrast agent into the blood stream of the patient subject may be highly useful in visualizing the way in which chemicals placed into the blood are absorbed and washed out of various types of tissue. Such an investigation is known as pharmacokinetics as it relates to the study of the nature of movement of chemical substances through the bodily tissue. The process of analyzing the pharmacokinetics of the contrast agent by MRI is known as dynamic contrast-enhanced (DCE) MRI.

In particular, in performing DCE MRI, a first MR image may be acquired prior to the administration of the magnetic contrast agent and then subsequent MR images may be acquired at regular intervals as the contrast agent is absorbed and washed out of the tissue under investigation. The sequence of MR images may then be analyzed to profile the nature of the absorption and washout. It is known that benign and malignant lesions within the breast may exhibit distinct pharmacokinetic profiles and thus this analysis may be highly useful in identifying one or more regions of interest that are breast malignancy candidates. After the one or more candidates have been identified, advanced pharmacokinetics (PK) analysis may be performed on the DCE MRI image data to quantitatively describe the absorption and washout of the contrast agent (CA) into and out from the candidate regions of interest for the purposes of differentiating between malignant and benign lesions.

While existing approaches to PK analysis in DCE MRI may provide some level of characterizing candidate regions of interest, this data tends to be difficult to normalize, and as such, it may be exceedingly difficult to compare the PK analysis data across data sets from one or more patients and/or between various MR systems. This difficulty in performing such comparisons impairs the effectiveness of research such as population studies.

SUMMARY

A method for performing pharmacokinetic analysis in magnetic resonance (MR) images includes administering a dose of contrast agent (CA) into a subject. A sequence of medical images is acquired of the subject at set temporal intervals. The time-based behavior of concentrations of CA is described within the subject for each voxel of each medical image of the sequence of medical images based on a reference voxel using a compartmental model for pharmacokinetic analysis that is based on a set of compartmental model parameters. The compartmental model is solved for each of the compartmental model parameters. The solution for the compartmental model parameters is used to estimate one or more parameters of physiological significance.

The contrast agent may include gadolinium. The medical image data may include magnetic resonance (MR) image data and the sequence of medical images is part of a dynamic contrast-enhanced (DCE) MRI. Alternatively, or additionally, the medical image data may include computed tomography (CT) image data and/or ultrasound image data.

The sequence of medical images may be part of a dynamic contrast-enhanced (DCE) MRI. The compartmental model for performing pharmacokinetic analysis may be the Mohan-Shingawa model given by the equation: $c_T(t)=(A_1 e^{-B_1 t}+A_2 e^{-B_2 t})*c_R(t)+A_3 c_R(t)$, where $c_T(t)$ denotes the concentration at the voxel being analyzed, $c_R(t)$ denotes the concentration at the reference voxel, and $A_1$, $B_1$, $A_2$, $B_2$, and $A_3$ denote the parameters of the compartmental model.

The one or more parameters of physiological significance may be the Tofts parameters: $v_p$, $K^{trans}$ and $k_{ep}$, wherein $v_p$ represents a ratio of plasma to a unit volume, $K^{trans}$ represents a rate of absorption into the tissue, for example, the extravascular extracellular space (EES), and $k_{ep}$ represents a rate of washout.

The solution for the compartmental model parameters may be used to estimate one or more parameters of physiological significance includes assuming a value of maximum enhancement is equal to the total dose of the contrast agent administered to the subject.

Solving the compartmental model for each of the compartmental model parameters may include expressing each of the compartmental model parameters as a function of the one or more parameters of physiological significance.

The compartmental model for performing pharmacokinetic analysis may be the Mohan-Shingawa model given by the equation: $c_T(t)=(A_1 e^{-B_1 t}+A_2 e^{-B_2 t})*c_R(t)+A_3 c_R(t)$, where $c_T(t)$ denotes the concentration at the voxel being analyzed, $c_R(t)$ denotes the concentration at the reference voxel, and $A_1$, $B_1$, $A_2$, $B_2$, and $A_3$ denote the parameters of the compartmental model, wherein the one or more parameters of physiological significance are the Tofts parameters: $v_p$, $K^{trans}$ and $k_{ep}$, wherein $v_p$ represents a ratio of a ratio of plasma to a unit volume, $K^{trans}$ represents a rate of absorption into the EES, and $k_{ep}$ represents a rate of washout, all with respect to the voxel of the medical image, and $v_p^R$, $K^{trans^R}$ and $k_{ep}^R$, wherein $v_p^R$ represents a ratio of tissue to plasma, $K^{trans^R}$ represents a rate of absorption into the tissue and $k_{ep}^R$ represents a rate of washout, all with respect to the reference voxel, wherein the Toft parameters relate to the Tofts model, which is expressed as:

$$C_t(t) = v_p c_p(t) + K^{trans} c_p(t) * e^{-k_{ep} t} \text{ and}$$

$$C_R(t) = v_p^R c_p(t) + K^{trans^R} c_p(t) * e^{-k_{ep}^R t}$$

where $c_p(t)$ denotes an arterial input function (AIF), and wherein expressing each of the compartmental model parameters as a function of the one or more parameters of physiological significance yields the following expressions:

$$v_p = A_3 v_p^R$$
$$K^{trans} = A_2 \frac{B_1 - B_2}{k_{ep}^R - B_2} v_p^R$$
$$k_{ep} = B_2$$
$$K^{trans^R} = (B_1 - k_{ep}^R) v_p^R$$

Here, $v_p^R$ may be estimated as the maximum enhancement of $v_p^R c_p(t)$ over the administered dose of CA.

A method for detecting a malignant lesion includes administering a dose of contrast agent (CA) into a subject. A sequence of medical images is acquired of the subject at set temporal intervals. A lesion candidate is identified based on the acquired sequence of medical images. The time-based behavior of concentrations of CA within the subject is described for each voxel of each medical image of the sequence of medical images based on a reference voxel using a compartmental model for pharmacokinetic analysis that is based on a set of compartmental model parameters. The compartmental model is solved for each of the compartmental model parameters. The solution for the compartmental model parameters is used to estimate one or more parameters of physiological significance. It is determined whether the identified lesion candidate is a malignant lesion based on the described time-based behavior of concentrations of CA and the estimated parameters of physiological significance.

The compartmental model for performing pharmacokinetic analysis may be the Mohan-Shingawa model given by the equation: $c_T(t) = (A_1 e^{-B_1 t} + A_2 e^{-B_2 t}) * c_R(t) + A_3 c_R(t)$, where $c_T(t)$ denotes the concentration at the voxel being analyzed, $c_R(t)$ denotes the concentration at the reference voxel, and $A_1$, $B_1$, $A_2$, $B_2$, and $A_3$ denote the parameters of the compartmental model.

The one or more parameters of physiological significance may be the Tofts parameters: $v_p$, $K^{trans}$ and $k_{ep}$, wherein v represents a ratio of plasma to a unit volume, $K^{trans}$ represents a rate of absorption into the EES, and $k_{ep}$ represents a rate of washout.

The solution for the compartmental model parameters may be used to estimate one or more parameters of physiological significance includes assuming a value of maximum enhancement is equal to the total dose of the contrast agent administered to the subject.

The compartmental model may be solved for each of the compartmental model parameters includes expressing each of the compartmental model parameters as a function of the one or more parameters of physiological significance.

The compartmental model for performing pharmacokinetic analysis may be the Mohan-Shingawa model given by the equation: $c_T(t) = (A_1 e^{-B_1 t} + A_2 e^{-B_2 t}) * c_R(t) + A_3 c_R(t)$, where $c_T(t)$ denotes the concentration at the voxel being analyzed, $c_R(t)$ denotes the concentration at the reference voxel, and $A_1$, $A_2$, $B_2$, and $A_3$ denote the parameters of the compartmental model, wherein the one or more parameters of physiological significance are the Tofts parameters: $v_p$, $K^{trans}$ and $k_{ep}$, wherein $v_p$ represents a ratio of plasma to a unit, $K^{trans}$ represents a rate of absorption into the EES, and $k_{ep}$ represents a rate of washout, all with respect to the voxel of the medical image, and $v_p^R$, $K^{trans^R}$ and $k_{ep}^R$, wherein $v_p^R$ represents a ratio of tissue to plasma, $K^{trans^R}$ represents a rate of absorption into the tissue, and $k_{ep}^R$ represents a rate of washout, all with respect to the reference voxel, wherein the Toft parameters relate to the Tofts model, which is expressed as:

$$C_T(t) = v_p c_p(t) + K^{trans} c_p(t) * e^{-k_{ep} t} \text{ and}$$

$$C_R(t) = v_p^R c_p(t) + K^{trans^R} c_p(t) * e^{-k_{ep}^R t}$$

where $c_p(t)$ denotes an arterial input function (AIF), and wherein expressing each of the compartmental model parameters as a function of the one or more parameters of physiological significance yields the following expressions:

$$v_p = A_3 v_p^R$$
$$K^{trans} = A_2 \frac{B_1 - B_2}{k_{ep}^R - B_2} v_p^R$$
$$k_{ep} = B_2$$
$$K^{trans^R} = (B_1 - k_{ep}^R) v_p^R$$

Here, $v_p^R$ may be estimated as the maximum enhancement of $v_p^R c_p(t)$ over the administered dose of CA.

A computer system includes a processor and a program storage device readable by the computer system, embodying a program of instructions executable by the processor to perform method steps for performing pharmacokinetic analysis in magnetic resonance (MR) images. The method includes administering a dose of contrast agent (CA) into a subject. A sequence of magnetic resonance images are acquired of the subject at set temporal intervals. The time-based behavior of concentrations of CA within the subject is described for the sequence of magnetic resonance images using a compartmental model for pharmacokinetic analysis that is based on a set of compartmental model parameters. The compartmental model is solved for each of the compartmental model parameters. The solution for the compartmental model parameters may be used to estimate one or more parameters of physiological significance.

The compartmental model for performing pharmacokinetic analysis may be the Mohan-Shingawa model given by the equation: $c_T(t) = (A_1 e^{-B_1 t} + A_2 e^{-B_2 t}) * c_R(t) + A_3 c_R(t)$, where $c_T(t)$ denotes the concentration at a voxel being analyzed, $c_R(t)$ denotes the concentration at a reference voxel, and $A_1$, $B_1$, $A_2$, $B_2$, and $A_3$ denote the parameters of the compartmental model.

The one or more parameters of physiological significance may be the Tofts parameters: $v_p$, $K^{trans}$ and $k_{ep}$.

The solution for the compartmental model parameters may be used to estimate one or more parameters of physiological significance includes assuming a value of maximum enhancement is equal to the total dose of the contrast agent administered to the subject.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

Figure 1:
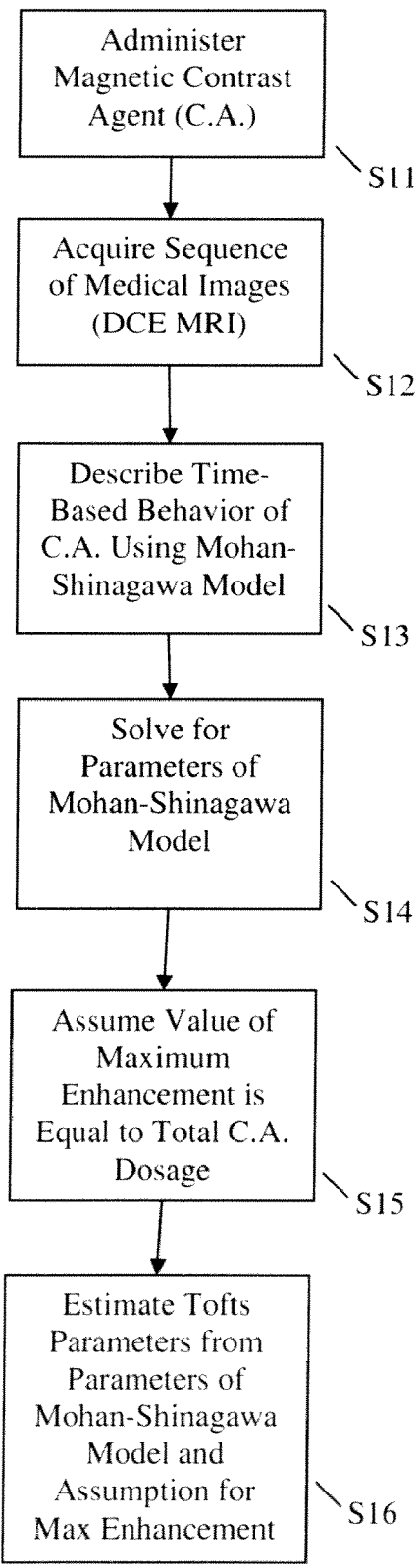
FIG. 1 is a flowchart illustrating a method for performing pharmacokinetic analysis in magnetic resonance (MR) images according to an exemplary embodiment of the present invention.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention seek to provide an approach for quantitatively analyzing PK data in DCE MRIs in a manner that may be easily compared across various data sets that include multiple patients and/or various MR systems. This may be achieved, for example, by normalizing the PK analysis data in a manner that is independent of a choice of reference region; unlike existing approaches for PK analysis which are highly dependent upon the reliability and accuracy of the selection of a reference region from which PK analysis is based around.

Pharmacokinetic (PK) analysis may be broadly characterized according to either a compartmental model or a heuristic model. The compartmental model attempts to describe the microscopic view of the breast tissue as a set of compartments and then models the interaction between the compartments of the set with respect to the nature of the absorption and washout of the contrast agent (CA). Various techniques making use of a compartmental model may use different numbers of compartments to model the tissue and may use different equations to describe the movement of the CA.

Heuristic models for PK analysis attempt to model the absorption and washout phenomena as growing and/or decaying exponentials and may, for example, quantify the observed exponential changes.

Exemplary embodiments of the present invention may be characterized as a novel approach to compartmental modeling. In describing the model of the exemplary embodiment, it may be helpful to first consider the Tofts model. The Tofts model is a commonly used compartmental model for PK analysis. In the Tofts model, a reference region is selected to aid in the estimation of the arterial input function (AIF), which represents a rate of blood flow through the left ventricle of the heart. According to the Tofts model, the time-behavior of the concentration of CA at the voxel under analysis and the reference voxel may be described in terms of the following equations:

$$C_T(t) = v_p c_p(t) + K^{trans} c_p(t) * e^{-k_{ep} t} \quad (1)$$

$$C_R(t) = v_p^R c_p(t) + K^{trans^R} c_p(t) * e^{-k_{ep}^R t} \quad (2)$$

where $c_p(t)$ denotes the true AIF, $v_p$, $K^{trans}$ and $k_{ep}$ are the Tofts model parameters for the voxel being analyzed and $v_p^R$, $K^{trans^R}$ and $k_{ep}^R$ are the Tofts model parameters for the reference voxel. As used herein, model parameters including the R exponent are representative of the reference voxel, unless otherwise specified.

These Tofts parameters have physiological significance. For example, $K^{trans}$ represents the rate of absorption in which blood flows into the tissue, for example, the extravascular extracellular space (EES), $k_{ep}$ represents the rate of washout in which blood leaves the tissue, and $v_p$ represents the ratio of the plasma that surrounds the tissue to a unit volume. Each of these Toft parameters, having physiological significance, may have a high degree of diagnostic value.

Exemplary embodiments of the present invention utilize a modification of the Tofts model known as the Mohan-Shinagawa model. This approach makes use of the fact that the AIF represents the concentration of the CA being fed into the tissue under analysis. This approach may then utilize the concept of a reference region to relate the concentration of the CA at a voxel under analysis to that of the reference voxel, rather than the AIF, as is often done in the art. Then, with the reference region being selected uniformly across data sets from different patients and different MR acquisition systems, the model parameters of this approach may be more easily and uniformly normalized and malignant lesions may then be more accurately localized and false positives may be reduced. Additionally, population studies examining diverse sets of PK analysis data may be facilitated by the greater uniformity of data.

The Mohan-Shinagawa model describes the time-behavior of the concentration of contrast agent (CA) at a voxel under analysis, with respect to the time-behavior of the concentration of CA at the reference mode. The Mohan-Shingawa model may be expressed as the following equation:

$$c_T(t) = (A_1 e^{-B_1 t} + A_2 e^{-B_2 t}) * c_R(t) + A_3 c_R(t) \quad (?)$$

where $c_T(t)$ denotes the concentration at the voxel being analyzed, $c_R(t)$ denotes the concentration at the reference voxel, and $A_1$, $B_1$, $A_2$, $B_2$, and $A_3$ denote the parameters of the Mohan-Shingawa model.

While the Mohan-Shingawa model may provide better normalization across multiple patients and image acquisition systems and better discrimination between malignant and benign lesions than the Tofts model, and extensions thereof, the parameters of the Mohan-Shinagawa model may be more complex than those of the Tofts model, and may lack the physiological significance of the parameters of the Tofts model. To illustrate this point, the parameters for the Mohan-Shinagawa model are expressed below as functions of the Tofts model parameters at the two voxels, the voxel under analysis and the reference voxel:

$$A_1 = \frac{K^{trans^R}}{v_p^R(k_{ep} - k_{ep}^R) - K^{trans^R}} \cdot \frac{v_p(k_{ep}^R v_p^R + K^{trans}) - v_p^R(k_{ep} v_p + K^{trans})}{v_p^{R2}} \quad (3)$$

$$B_1 = k_{ep}^R + \frac{K^{trans^R}}{v_p^R}$$

$$A_2 = \frac{(k_{ep}^R - k_{ep}) K^{trans}}{v_p^R(k_{ep}^R - k_{ep}) + (K^{trans^R})}$$

$$B_2 = k_{ep}$$

$$A_3 = \frac{v_p}{v_p^R}$$

For additional description concerning the Tofts model, the Mohan-Shinagawa model and their application to PK analysis, one may refer to the co-pending and co-assigned U.S. patent application Ser. No. 12/181,396, filed Jul. 29, 2008, which is hereby incorporated by reference in its entirety.

In light of the benefits of utilizing the Mohan-Shinagawa model over the Tofts model, it may be desirable to utilize the Mohan-Shinagawa model for acquiring PK data for performing patient diagnosis and for performing population studies across multiple patients and/or imaging systems. However, because of the complexity of the Mohan-Shinagawa parameters and their relatively low physiological significance, with respect to the Tofts parameters, exemplary embodiments of the present invention seek to provide a framework for estimating the physiologically significant Tofts model parameters from the Mohan-Shinagawa model parameters.

Even though the parameters of the Mohan-Shinagawa model are functions of the Tofts model parameters for the two voxels used, the voxel under analysis and the reference voxel, it may be difficult to estimate the Tofts model parameters from the Mohan-Shinagawa model parameters. This is at least because there are five Mohan-Shinagawa model parameter equations which must be used to solve for six Toft model parameters (the $v_p$, $K^{trans}$ and $k_{ep}$ parameters for the voxel under analysis and the reference voxel). Because one cannot solve for six unknowns using five equations, there is no obvious way known in the art of quickly and efficiently estimating the Mohan-Shinagawa model parameters from the Tofts model parameters.

Absolute Tofts model parameters would describe the physiological attributes of blood flow in and out of the tissue along with the ratio of tissue to plasma. e Mohan-Shinagawa model parameters are functions of these ideal Tofts model parameters and hence, irrespective of the choice of a reference region, if the model equations for the Mohan-Shinagawa model parameters could be inverted so as to estimate the Tofts model parameters from the Mohan-Shinagawa model parameters, since all quantities used are from the available dataset, with ideal error-free estimation, the obtained values would be the exact Tofts model parameters. Additionally, the resulting Tofts model parameters would describe the voxel concentrations absolutely and hence the dependence on the choice of reference region would be eliminated, while the AIF would still not have to be estimated.

However, as indicated above, the primary issue in estimating the Tofts model parameters though the Mohan-Shinagawa model parameters is that the latter only yields five parameters while in all, there are six values to be estimated for the extended Tofts model. Accordingly, exemplary embodiments of the present invention seek to introduce some form of redundancy, for example, by using multiple voxels, or by using some additional data.

The Mohan-Shinagawa model parameters are related to the parameters for the Tofts model at the voxel under analysis and the reference voxel as expressed above in equations (3). These equations may be solved to obtain expressions for the various individual Tofts model parameters. This simplification yields the following expressions:

$$v_p = A_3 v_p^R \quad (4)$$

$$K^{trans} = A_2 \frac{B_1 - B_2}{k_{ep}^R - B_2} v_p^R$$

$$k_{ep} = B_2$$

$$K^{trans^R} = (B_1 - k_{ep}^R) v_p^R$$

where $k_{ep}^R$ may be obtained by solving the following quadratic equation:

$$A_3 k_{ep}^{R^2} - k_{ep}^R(A_1 + A_2 + A_3 B_1 + A_3 B_2) + (A_1 B_2 + A_2 B_1 + A_3 B_1 B_2) = 0 \quad (5)$$

Solving this quadratic equation for $k_{ep}^R$ leads to the following expressions:

$$k_{ep}^R = \frac{-b \pm \sqrt{b^2 - 4ac}}{2a} \quad (6)$$

$$a = A_3$$

$$b = A_1 + A_2 + A_3 B_1 + A_3 B_2$$

$$c = A_1 B_2 + A_2 B_1 + A_3 B_1 B_2$$

Because inverting the equations for the Mohan-Shinagawa model parameters results in a quadratic equation, there are two possible solutions for $k_{ep}^R$. Moreover, the remaining quantities may be simplified by expressing them in terms of ratios with respect to $v_p^R$. While the quantities $$\frac{K^{trans}}{v_p}$$

and $k_{ep}^R$ may have physiological significance and may be used in rendering diagnoses, the challenge remains to determine $v_p$ or $v_p^R$ and $K^{trans}$ or $K^{trans^R}$.

The quantities $v_p$ or $v_p^R$ and $K_{trans}$ or $K^{trans^R}$ both multiply terms containing the AIF in the Tofts model expression. Thus, even with the use of the above expressions, the quantities of interest may only be estimated in terms of $v_p^R$. Since the AIF itself is also unknown at this point, there are still two remaining unknowns in the Tofts model expressions. Without additional information, separating out these two quantities may not be possible.

Exemplary embodiments of the present invention may rely on the fact that the dosage of CA injected into each patient is known information. By appreciating that the AIF is the concentration of CA fed into the tissue of interest, it may be implied that the maximum value that the AIF can take is the maximum density of CA in the blood proportional in the ideal situation to the injection dosage itself This implication may thus be used in computing $v_p^R$ and, by extension, all of the Tofts model parameters for all of the voxels under analysis.

These calculations may begin with the form of the expression for the CA concentration at the reference voxel, represented according to the following expressions:

$$c_R(t) = v_p^R \left( c_p(t) + \frac{K^{trans^R}}{v_p^R} e^{-k_{ep}t} * c_p(t) \right) \quad (7)$$

$$= v_p^R c_p(t) * \left( del(t) + \frac{K^{trans^R}}{v_p^R} e^{-k_{ep}t} \right)$$

Since the quantities $$\frac{k^{trans^R}}{v_p^R}$$

and $k_{ep}^R$ are known, deconvolution may be used to estimate $s(t)=v_p^R c_p(t)$. This may be expressed according to the following expression:

$$s(t) = v_p^R c_p(t) \quad (8)$$
$$= c_R(t) - k_r e^{-\left(k_R + k_{ep}^R\right)} * c_R(t)$$

where, $$k_R = \frac{k^{transR}}{v_p^R} \quad (9)$$

Here, the theoretical maximum enhancement of this signal may be $v_p^R D$ where D is the maximum density of arriving at the tissue. Accordingly, $$v_p^R = \frac{MaximumEnhancement(s(t))}{D} \quad (10)$$

Next, this estimated value for $v_p^R$ may be used to estimate the remaining Tofts model parameters, for example, using the equations (4) discussed above.

As discussed above, $k_{ep}^R$ may be obtained by solving the quadratic equation (5). However, estimation of the Mohan-Shinagawa model parameters may not be completely error free, and as a result, even with the same reference voxel used throughout the analysis for a given image, the quadratic equation may yield different results for different voxels. Exemplary embodiments of the present invention may solve this problem by weighing the $k_{ep}^R$ value yielded at each voxel with the lowest estimation error.

Moreover, according to exemplary embodiments of the present invention, because the exact dosage of CA administered to the patient may be used in estimating $v_p^R$, where the exact administered dosage cannot be definitively known, it may be estimated based on the value of maximum enhancement in each given image.

FIG. 1 is a flowchart illustrating a method for performing pharmacokinetic analysis in magnetic resonance (MR) images according to an exemplary embodiment of the present invention. First, the magnetic contrast agent (CA) may be administered to the patient subject (Step S11). As mentioned above, the CA may be a gadolinium-based agent. The CA may be injected directly into the bloodstream of the patient subject.

A sequence of medical images may then be acquired (Step S12). The sequence may be, for example, a DCE MRI. The DCE MRI may actually involve the acquisition of a first image that is taken prior to the administration of the CA in Step S11. Subsequent images may be acquired at regular intervals in time that follow the administration of the CA. For example, an image may be acquired once every minute for a predetermined number of minutes.

After the medical image sequence has been acquired, the image sequence may be analyzed to describe the time-based behavior of the CA as it is taken up and washed out of the image voxels (Step S13). As discussed above, exemplary embodiments of the present invention may model the behavior using the Mohan-Shinagawa model, which may be represented as a function of multiple Mohan-Shinagawa model parameters. While representation in accordance with the Mohan-Shinagawa model may provide superior results to alternative modeling techniques such as the Tofts model, for example, improved ability to be normalized and fairly compared with similar quantitative results across multiple patients and multiple different image acquisition and processing systems, the parameters of the Mohan-Shinagawa model may lack the physiological significance of the Tofts model parameters. Accordingly, it may be desirable to calculate and or estimate the Tofts model parameters from the Mohan-Shinagawa model parameter.

In order to determine the Tofts model parameters, it may first be helpful to solve for the parameters of Mohan-Shinagawa model (Step S14). Thus, the expressions of the Mohan-Shinagawa model may be arranged into equations for each of the Mohan-Shinagawa models, for example, as a function of the Tofts model parameters.

Because at this point, there may be more variables to solve for than there are expressions of the Mohan-Shinagawa model parameters, it may not be possible to accurately solve for each Tofts model parameter without introducing additional data. This additional data may be gained, for example, by assuming that a value of maximum enhancement of each image is equal to the total dose of CA that has been administered to the patent back in Step S11 (Step S15). Using this information, the Tofts model parameters may then be estimated from the expressions of the Mohan-Shinagawa model parameters and the assumption of the value of maximum enhancement (Step S16). In this way, the enhanced characteristics of the Mohan-Shinagawa model may be enjoyed while still determining the Tofts model parameters, which are of physiological value. The Tofts model parameters may then be considered in rendering a diagnosis and/or in collecting data for subsequent studies.

Figure 2:
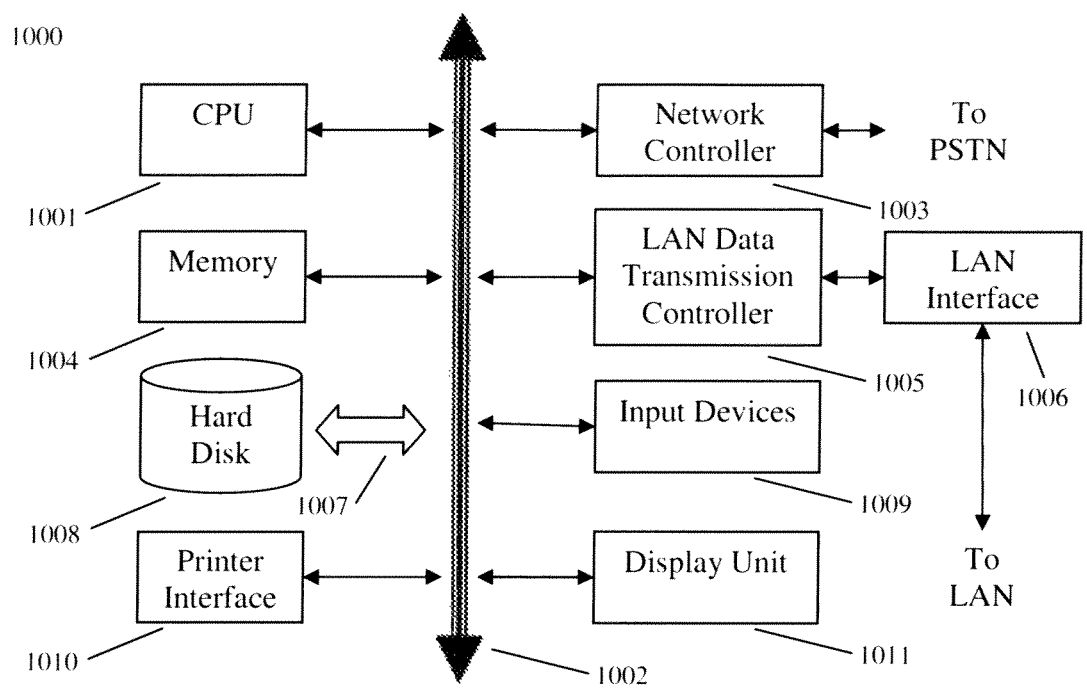
FIG. 2 shows an example of a computer system capable of implementing the method and apparatus according to embodiments of the present disclosure.

FIG. 2 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and or features of different exemplary embodiments may be combined with each other and/or substituted for each other within the scope of this disclosure and appended claims.

What is claimed is:

1. A method for performing pharmacokinetic analysis in medical image data, comprising: administering a dose of contrast agent (CA) into a subject; acquiring a sequence of medical images of the subject at set temporal intervals, the medical image data being one of: magnetic resonance (MR) image data, computed tomography (CT) data, and ultrasound image data; describing the time-based behavior of concentrations of CA within the subject for each voxel of each medical image of the sequence of medical images based on a reference voxel using a compartmental model for pharmacokinetic analysis that is based on a set of compartmental model parameters; solving the compartmental model for each of the compartmental model parameters; and using the solution for the compartmental model parameters to estimate one or more parameters of physiological significance, wherein using the solution for the compartmental model parameters to estimate one or more parameters of physiological significance includes assuming a value of maximum enhancement is equal to the total dose of the contrast agent administered to the subject.

2. The method of claim 1, wherein the contrast agent includes gadolinium.

3. The method of claim 1, wherein the medical image data includes magnetic resonance (MR) image data and the sequence of medical images is part of a dynamic contrast-enhanced (DCE) MRI.

4. The method of claim 1, wherein the compartmental model for performing pharmacokinetic analysis is the Mohan-Shingawa model given by the equation: $c_T(t)=(A_1 e^{-B_1 t}+A_2 e^{-B_2 t})*c_R(t)+A_3 c_R(t)$, where $c_T(t)$ denotes the concentration at the voxel being analyzed, $c_R(t)$ denotes the concentration at the reference voxel, and $A_1$, $B_1$, $A_2$, $B_2$, and $A_3$ denote the parameters of the compartmental model.

5. The method of claim 1, wherein the one or more parameters of physiological significance are the Tofts parameters: $v_p$, $K^{trans}$ and $k_{ep}$, wherein $v_p$ represents a ratio of tissue to plasma, $K^{trans}$ represents a rate of absorption into the tissue, and $k_{ep}$ represents a rate of washout.

6. The method of claim 1, wherein solving the compartmental model for each of the compartmental model parameters includes expressing each of the compartmental model parameters as a function of the one or more parameters of physiological significance.

7. The method of claim 6, wherein the compartmental model for performing pharmacokinetic analysis is the Mohan-Shingawa model given by the equation: $c_T(t)=A_1 e^{-B_1 t}+A_2 e^{-B_2 t})*c_R(t)+A_3 c_R(t)$, where $c_T(t)$ denotes the concentration at the voxel being analyzed, $c_R(t)$ denotes the concentration at the reference voxel, and $A_1$, $B_1$, $A_2$, $B_2$, and $A_3$ denote the parameters of the compartmental model, wherein the one or more parameters of physiological significance are the Tofts parameters: $v_p$, $K^{trans}$ and $k_{ep}$, wherein $v_p$ represents a ratio of plasma to a unit volume, $K^{trans}$ represents a rate of absorption into the extravascular extracellular space and $k_{ep}$ represents a rate of washout, all with respect to the voxel of the medical image, and $v_p^R$, $K^{trans R}$ and $k_{ep}^R$, wherein $v_p^R$ represents a ratio of plasma to a unit volume, $K^{trans R}$ represents a rate of absorption into the extravascular extracellular space, and $k_{ep}^R$ represents a rate of washout, all with respect to the reference voxel, wherein the Toft parameters relate to the Toft model, which is expressed as:

$$C_T(t)=v_p c_p(t)+K^{trans} c_p(t)*e^{-k_{ep} t} \text{ and}$$

$$C_R(t)=v_p^R c_p(t)+K^{trans R} c_p(t)*e^{-k_{ep}^R t}$$

where $c_p(t)$ denotes an arterial input function (AIF), and
wherein expressing each of the compartmental model parameters as a function of the one or more parameters of physiological significance yields the following expressions:

$$v_p = A_3 v_p^R$$

$$K^{trans} = A_2 \frac{B_1 - B_2}{k_{ep}^R - B_2} v_p^R$$

-continued $$k_{ep} = B_2$$

$$K^{trans R} = (B_1 - k_{ep}^R) v_p^R$$

8. The method of claim 7, wherein $v_p^R$ is estimated as the maximum enhancement of $v_p^R c_p(t)$ over the administered dose of CA.

9. A method for detecting a malignant lesion, comprising: administering a dose of contrast agent (CA) into a subject; acquiring a sequence of medical images of the subject at set temporal intervals, wherein the series of medical images are one of: magnetic resonance (MR) images, computed tomography (CT) images, and ultrasound images; identifying a lesion candidate based on the acquired sequence of medical images; describing the time-based behavior of concentrations of CA within the subject for each voxel of each medical image of the sequence of medical images based on a reference voxel using a compartmental model for pharmacokinetic analysis that is based on a set of compartmental model parameters; solving the compartmental model for each of the compartmental model parameters; using the solution for the compartmental model parameters to estimate one or more parameters of physiological significance; and determining whether the identified lesion candidate is a malignant lesion based on the described time-based behavior of concentrations of CA and the estimated parameters of physiological significance, wherein using the solution for the compartmental model parameters to estimate one or more parameters of physiological significance includes assuming a value of maximum enhancement is equal to the total dose of the contrast agent administered to the subject.

10. The method of claim 9, wherein the compartmental model for performing pharmacokinetic analysis is the Mohan-Shingawa model given by the equation: $c_T(t)=(A_1 e^{-B_1 t}+A_2 e^{-B_2 t})*c_R(t)+A_3 c_R(t)$, where $c_T(t)$ denotes the concentration at the voxel being analyzed, $c_R(t)$ denotes the concentration at the reference voxel, and $A_1$, $B_1$, $A_2$, $B_2$, and $A_3$ denote the parameters of the compartmental model.

11. The method of claim 9, wherein the one or more parameters of physiological significance are the Toft parameters: $v_p$, $K^{trans}$ and $k_{ep}$, wherein $v_p$ represents a ratio of plasma to a unit volume, $K^{trans}$ represents a rate of absorption into the extravascular extracellular space, and $k_{ep}$ represents a rate of washout.

12. The method of claim 9, wherein solving the compartmental model for each of the compartmental model parameters includes expressing each of the compartmental model parameters as a function of the one or more parameters of physiological significance.

13. The method of claim 12, wherein the compartmental model for performing pharmacokinetic analysis is the Mohan-Shingawa model given by the equation: $c_T(t)=(A_1 e^{-B_1 t}+A_2 e^{-B_2 t})*c_R(t)+A_3 c_R(t)$, where $c_T(t)$ denotes the concentration at the voxel being analyzed, $c_R(t)$ denotes the concentration at the reference voxel, and $A_1$, $B_1$, $A_2$, $B_2$, and $A_3$ denote the parameters of the compartmental model, wherein the one or more parameters of physiological significance are the Tofts parameters: $v_p$, $K^{trans}$ and $k_{ep}$, wherein $v_p$ represents a ratio of plasma to a unit volume, $K^{trans}$ represents a rate of absorption into the extravascular extracellular space, and $k_{ep}$ represents a rate of washout, all with respect to the voxel of the medical image, and $v_p^R$, $K^{trans R}$ and $k_{ep}^R$, wherein $v_p^R$ represents a ratio of plasma to a unit volume, $K^{trans R}$ represents a rate of absorption into the extravascular extracellular space, and $k_{ep}^R$ represents a rate of washout, all with respect to the reference voxel,
wherein the Toft parameters relate to the Tofts model, which is expressed as:

$$C_T(t) = v_p c_p(t) + K^{trans} c_p(t) * e^{-k_{ep} t} \text{ and}$$

$$C_R(t) = v_p^R c_p(t) + K^{trans R} c_p(t) * e^{-k_{ep}^R t}$$

where $c_p(t)$ denotes an arterial input function (AIF), and wherein expressing each of the compartmental model parameters as a function of the one or more parameters of physiological significance yields the following expressions:

$$v_p = A_3 v_p^R$$

$$k^{trans} = A_2 \frac{B_1 - B_2}{k_{ep}^R - B_2} v_p^R$$

$$k_{ep} = B_2$$

$$k^{trans R} = (B_1 - k_{ep}^R) v_p^R$$

14. The method of claim 13, wherein $v_p^R$ is estimated as the maximum enhancement of $v_p^R c_p(t)$ over the administered dose of CA.

15. A computer system comprising: a processor; and a non-transitory computer readable media, embodying a program of instructions executable by the processor to perform method steps for performing pharmacokinetic analysis in magnetic resonance (MR) images, the method comprising: administering a dose of contrast agent (CA) into a subject; acquiring a sequence of magnetic resonance images of the subject at set temporal intervals; describing the time-based behavior of concentrations of CA within the subject for the sequence of magnetic resonance images using a compartmental model for pharmacokinetic analysis that is based on a set of compartmental model parameters; solving the compartmental model for each of the compartmental model parameters; and using the solution for the compartmental model parameters to estimate one or more parameters of physiological significance, wherein using the solution for the compartmental model parameters to estimate one or more parameters of physiological significance includes assuming a value of maximum enhancement is equal to the total dose of the contrast agent administered to the subject.

16. The computer system of claim 15, wherein the compartmental model for performing pharmacokinetic analysis is the Mohan-Shingawa model given by the equation: $c_T(t) = (A_1 e^{-B_1 t} + A_2 e^{-B_2 t}) * c_R(t) + A_3 c_R(t)$, where $c_T(t)$ denotes the concentration at a voxel being analyzed, $c_R(t)$ denotes the concentration at a reference voxel, and $A_1, B_1, A_2, B_2,$ and $A_3$ denote the parameters of the compartmental model.

17. The computer system of claim 15, wherein the one or more parameters of physiological significance are the Tofts parameters: $v_p$, $K^{trans}$ and $k_{ep}$.

* * * * *